(12) United States Patent
Del Biondi et al.

(10) Patent No.: US 11,839,773 B2
(45) Date of Patent: Dec. 12, 2023

(54) ITEM OF FOOTWEAR FOR MAGNETOTHERAPY

(71) Applicant: ALBERTO DEL BIONDI S.P.A., Noventa Padovana (IT)

(72) Inventors: Alberto Del Biondi, Padua (IT); Alessio Ivan Rizzi, Caselle di Santa Maria di Sala (IT)

(73) Assignee: ALBERTO DEL BIONDI S.P.A., Noventa Padovana (IT)

( * ) Notice: Subject to any disclaimer, the term of this patent is extended or adjusted under 35 U.S.C. 154(b) by 888 days.

(21) Appl. No.: 16/482,124

(22) PCT Filed: Jan. 30, 2018

(86) PCT No.: PCT/IB2018/050570
§ 371 (c)(1),
(2) Date: Jul. 30, 2019

(87) PCT Pub. No.: WO2018/138707
PCT Pub. Date: Aug. 2, 2018

(65) Prior Publication Data
US 2020/0001102 A1    Jan. 2, 2020

(30) Foreign Application Priority Data
Jan. 30, 2017   (IT) .................. 102017000009739

(51) Int. Cl.
*A61N 2/02* (2006.01)
*A43B 1/00* (2006.01)
(Continued)

(52) U.S. Cl.
CPC .............. *A61N 2/02* (2013.01); *A43B 1/0054* (2013.01); *A43B 3/34* (2022.01); *A43B 7/00* (2013.01);
(Continued)

(58) Field of Classification Search
CPC .......... A61N 2/00; A61N 2/002; A61N 2/004; A61N 2/006; A61N 2/008; A61N 2/02; A43B 1/0054; A43B 13/04; A43B 3/34
See application file for complete search history.

(56) References Cited

U.S. PATENT DOCUMENTS 5,285,586 A * 2/1994 Goldston ................. A43B 3/34
                                                        36/137
5,592,759 A * 1/1997 Cox ..................... A43B 1/0054
                                                        36/141
(Continued)

FOREIGN PATENT DOCUMENTS

EP        2532259 A2    12/2012
WO    2008109058 A1     9/2008
(Continued)

OTHER PUBLICATIONS

Written Opinion and International Search Report of PCT/IB2018/050570 dated Jun. 4, 2018.
IPRP of PCT/IB2018/050570 dated Jul. 30, 2019.

*Primary Examiner* — Carrie R Dorna
(74) *Attorney, Agent, or Firm* — Kristina Castellano; CASTELLANO PLLC

(57) ABSTRACT

An item of footwear for magnetotherapy comprises a lower sole in which there is defined a tread surface, an intermediate container which can be received in an opening which is defined in the lower sole, a magnetic field generator, a control unit, a battery, an inner sole which is or can be placed over the intermediate container and a vamp structure which is connected to the lower sole. The intermediate container is produced from material having greater rigidity with respect to the lower sole and comprises respective recesses which are intended to receive the magnetic field generator, the control unit and the battery, respectively.

20 Claims, 6 Drawing Sheets

(51) Int. Cl.
  *A43B 7/00*   (2006.01)
  *A43B 13/02*  (2022.01)
  *A43B 13/12*  (2006.01)
  *B29D 35/06*  (2010.01)
  *A43B 3/34*   (2022.01)
  *A61N 2/00*   (2006.01)

(52) U.S. Cl.
  CPC .......... *A43B 13/127* (2013.01); *B29D 35/061* (2013.01); *A61N 2/008* (2013.01)

(56) References Cited

U.S. PATENT DOCUMENTS

| | | | |
|---|---|---|---|
| 9,460,557 B1* | 10/2016 | Tran | G06T 15/205 |
| 2005/0187601 A1* | 8/2005 | Wang | A61H 39/04 |
| | | | 607/144 |
| 2009/0312449 A1* | 12/2009 | Sasaki | A43B 13/04 |
| | | | 525/98 |
| 2012/0199277 A1* | 8/2012 | Loveder | B29D 35/122 |
| | | | 156/60 |

FOREIGN PATENT DOCUMENTS

| | | | |
|---|---|---|---|
| WO | 2009135507 A1 | 11/2009 | |
| WO | 2015004498 A1 | 1/2015 | |

\* cited by examiner

ITEM OF FOOTWEAR FOR MAGNETOTHERAPY

CROSS REFERENCE TO RELATED APPLICATIONS

This application is a U.S. National Stage application of PCT/IB2018/050570 filed on Jan. 30, 2018, which claims priority to Italian patent application 102017000009739 filed on Jan. 30, 2017, the contents of both of which are incorporated herein by reference.

The invention relates to an item of footwear for magnetotherapy of the type including the characteristics set out in the preamble of the main claim.

In the context of medical footwear, there are known various solutions for the treatment of feet by means of magnetotherapy.

For example, the international patent application WO2008109058 describes a portable device for magnetotherapy which is integrated in an item of footwear.

In an embodiment, there are integrated in the inner sole of the item of footwear the winding which is intended to generate the magnetic field and a flexible circuit, while the battery and the control unit are arranged on the vamp and in the sole in the region of the heel.

In another embodiment, all the elements are incorporated in the inner sole which is received inside an item of footwear.

Another solution is described in the international patent application WO 2015/004498, in which the winding is incorporated in a support sole which is constructed from a rigid material while the battery is received inside a seat which is formed in the sole.

However, these known solutions have some disadvantages.

In general terms, all the known solutions have a structure which makes it very uncomfortable and therefore very unsuitable for being worn for long periods of time. The presence of components which are intended for the production of the magnetic field on the vamp or on the inner sole makes the item of footwear very uncomfortable in fact, while the presence thereof on the sole influences the movement of the foot during walking in a negative manner.

Conversely, it would be desirable for the item of footwear to be provided with comfort and in general structural characteristics so as to be able to be worn without trouble for an entire day and to be used in place of a conventional item of footwear.

The technical problem addressed by the present invention is to provide an item of footwear for magnetotherapy which is structurally and functionally configured for overcoming one or more of the limitations set out above with reference to the cited prior art.

In the context of the above-mentioned problem, a main object of the invention is to develop an item of footwear which has characteristics similar to those of a conventional item of footwear, both in aesthetic terms and in terms of comfort, while being provided with a piece of equipment for magnetotherapy.

This problem is solved and this object is achieved by the present invention by means of an item of footwear which is constructed according to claim 1.

Preferred characteristics of the invention are defined in the dependent claims.

The item of footwear according to the present invention ensures a high level of comfort for the user, at least partially preventing the presence of the internal components from being perceived during use of the item of footwear.

Furthermore, all the components necessary for the administration of the magnetic therapy can be received in a precise manner, ensuring ease of assembly of the item of footwear.

In addition, the particular combination of characteristics allows a reduction in the overall dimensions of the item of footwear, thereby allowing the production of an item of footwear which has good aesthetic characteristics and at the same time which is provided with magnetotherapeutic properties.

In fact, the use of a container for receiving the components required for the magnetotherapy allows them to be positioned and protected adequately, even using a sole having a thickness which is relatively small.

Furthermore, the lower sole can advantageously be formed by moulding, thereby allowing the construction of structures which may also be complex, notwithstanding the presence of the components which are responsible for the magnetotherapy.

The characteristics and the advantages of the invention will be better appreciated from the detailed description of two embodiments thereof which are illustrated by way of non-limiting example with reference to the appended drawings, in which.

Figure 6:
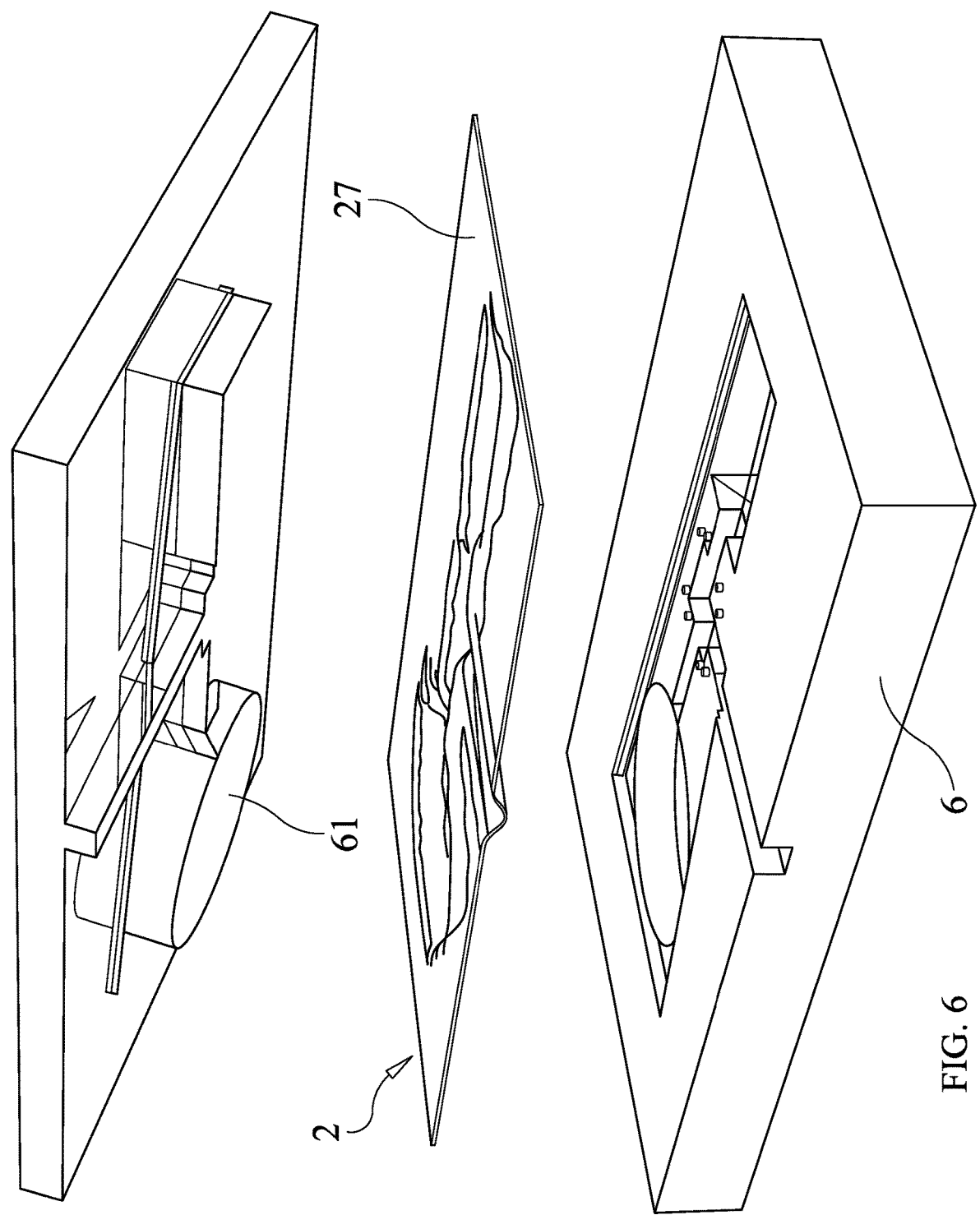
FIG. 6 is a perspective view which illustrates the premould of the intermediate container of FIG. 2 which is produced by means of a flexible and thermoformable film.
Figure 7:
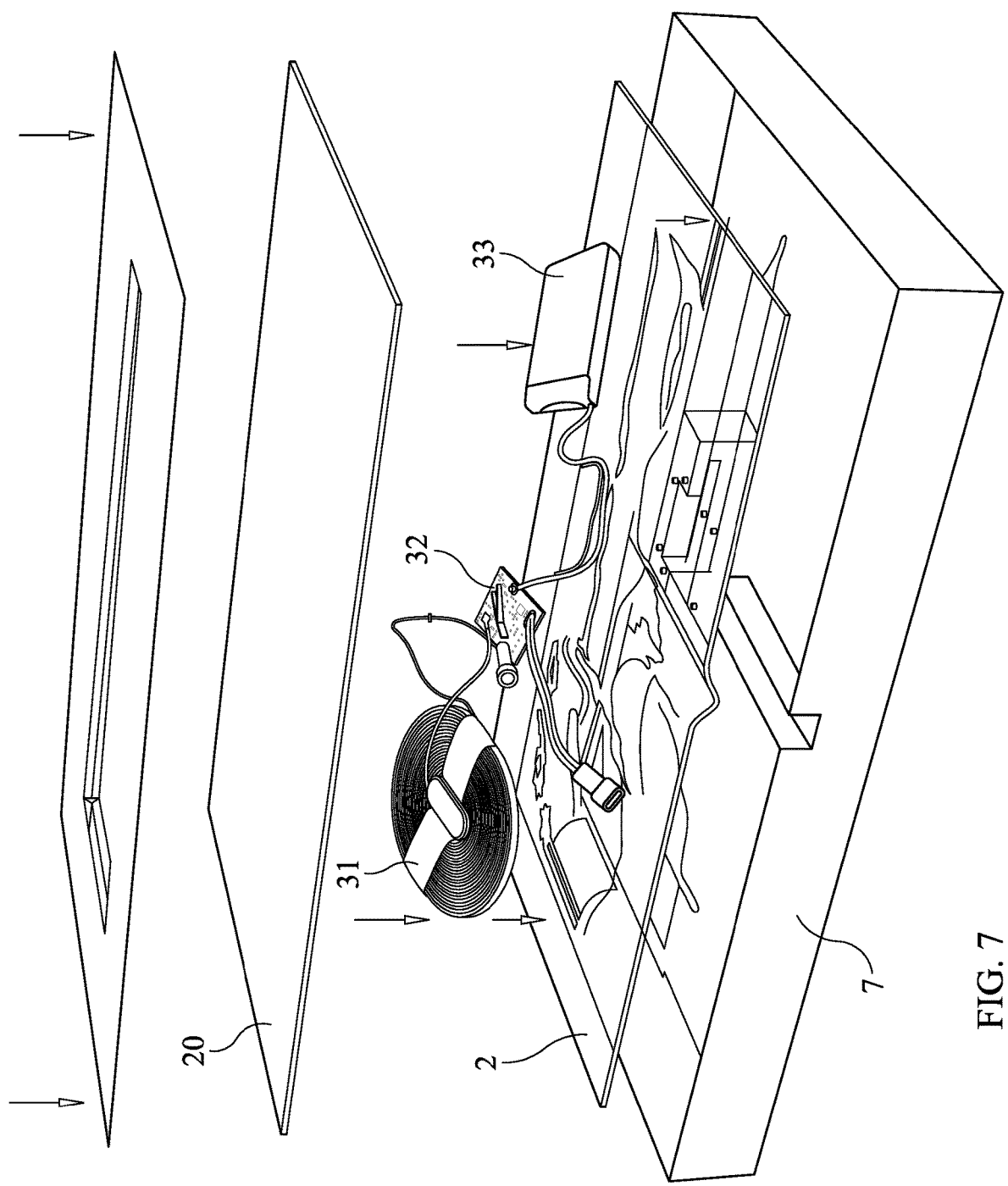
Figure 8A:
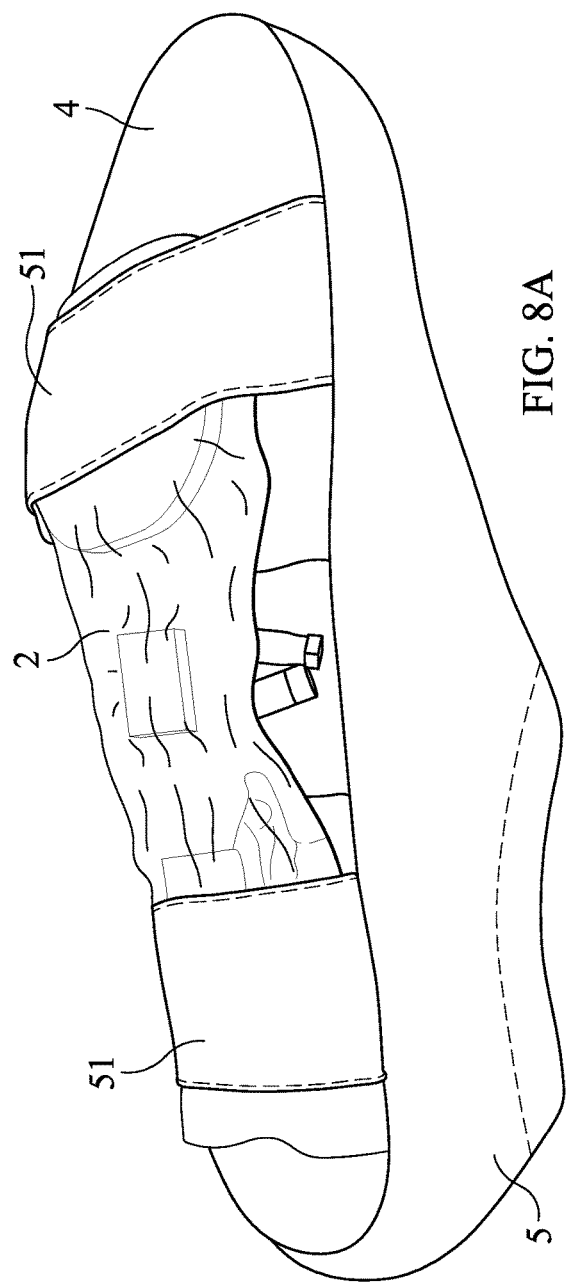
Figure 8B:
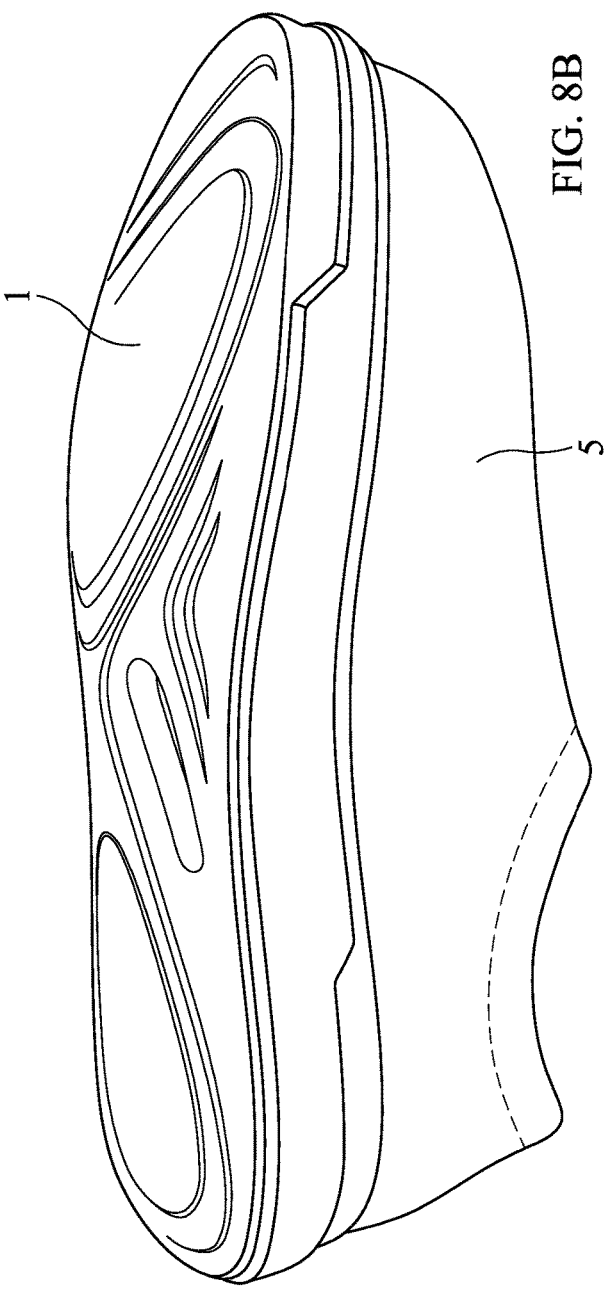

FIG. 7 is a perspective view which illustrates the assembly of the components for magnetotherapy in the container which is produced according to the process of FIG. 6 and to which there is applied a covering element; and FIGS. 8A and 8B are two perspective views which illustrate the positioning of the container with the components for magnetotherapy on a vamp structure and the subsequent respectively.

Figure 2:
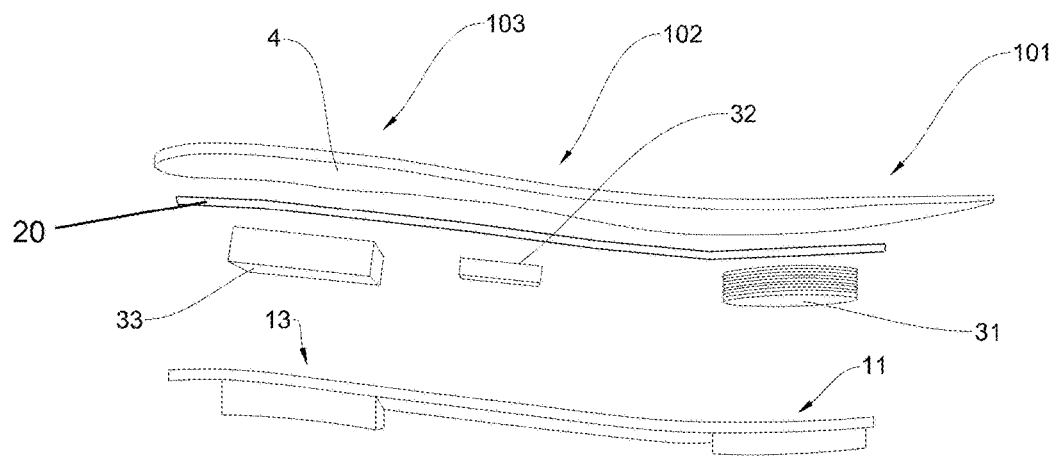
FIG. 2 is an exploded perspective side view of an intermediate container and components for magnetotherapy, with details of the item of footwear of FIG. 1.
Figure 1:
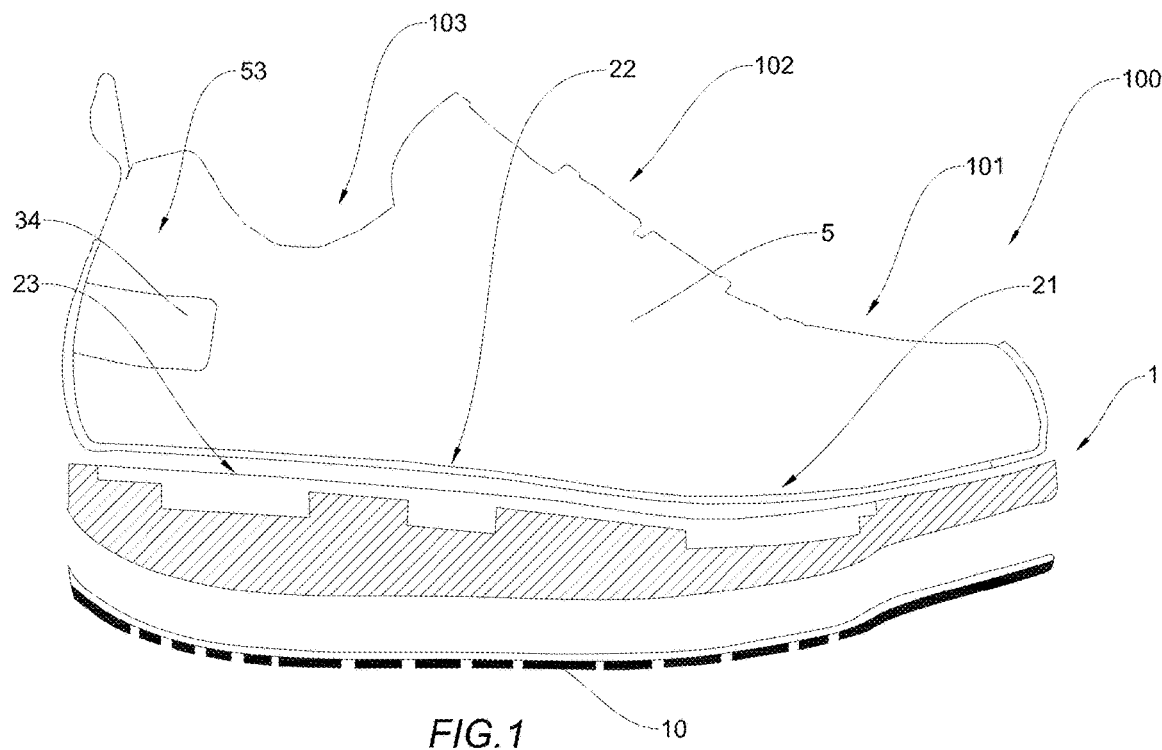
FIG. 1 is a side view of an item of footwear according to the present invention.

Initially with reference to FIG. 1, there is generally designated 100 an item of footwear for magnetotherapy which is formed according to the present invention.

The item of footwear 100 comprises a lower sole 1 and a vamp structure 5 which is connected thereto in a manner known per se. As can be seen in FIG. 1, the lower sole 1 extends longitudinally in a toe-to-heel direction which is designated X.

In the item of footwear 100, there are thus identified a forefoot zone 101, a mid-foot zone 102 and a rear foot zone 103, which are contiguous with respect to each other in the toe-to-heel direction X.

Preferably, the lower sole 1 is constructed from a material which is relatively resilient, for example, a polymer material. By way of example, the polymer material may be ethylene-vinyl acetate (EVA) or expanded thermosetting polyurethane (TPU).

Still with reference to FIG. 1, a tread surface 10 is defined or fixed in the lower sole 1 of the item of footwear 100.

In the context of the present invention, the term "tread surface 10" is intended to identify the surface of the sole 1 which is intended to be directed towards the sole during the use of the item of footwear. This surface could be constituted by the one directly in contact with the ground or this contact could be brought about by additional layers which are not illustrated in the Figures being interposed.

There is further defined in the lower sole 1 an opening 12 which is intended to receive an intermediate container 2, the function and the construction methods of which will be illustrated in greater detail below.

The item of footwear according to the present invention also comprises a magnetic field generator 31 which is actuated by a battery 33, preferably of the rechargeable type. To this end, there may be provided a recharging connector which extends through the inner sole or the lower sole, or a wireless recharging system, by means of a suitable recharging winding.

The magnetic field generator 31 is intended to generate a magnetic field in the region of one or more portions of the foot. The operation of the generator 31 is controlled by means of a control unit 32, by means of which it is possible for the magnetic field to be more suitable for the required therapeutic function.

In one embodiment, the control unit 32 is programmed in such a manner that the magnetic field generator has an intermittent function. In other words, when the generator is switched on, there alternate times in which the magnetic field is produced with times in which it is not produced. This functionality is found to be particularly advantageous because it allows an increase in the duration of the battery.

Figure 3A:
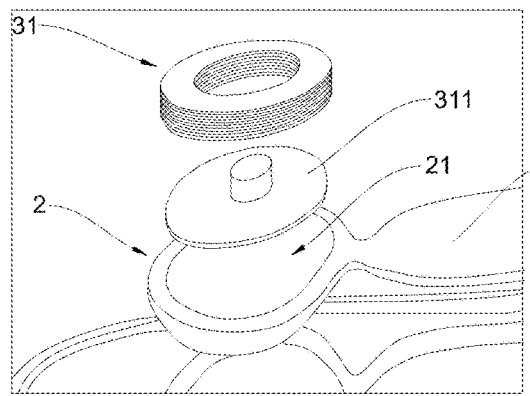
FIGS. 3 and 3A are an exploded perspective view and a relevant detail, from a different point of view, of the item of footwear of FIG. 1, without the relevant vamp.
Figure 3:
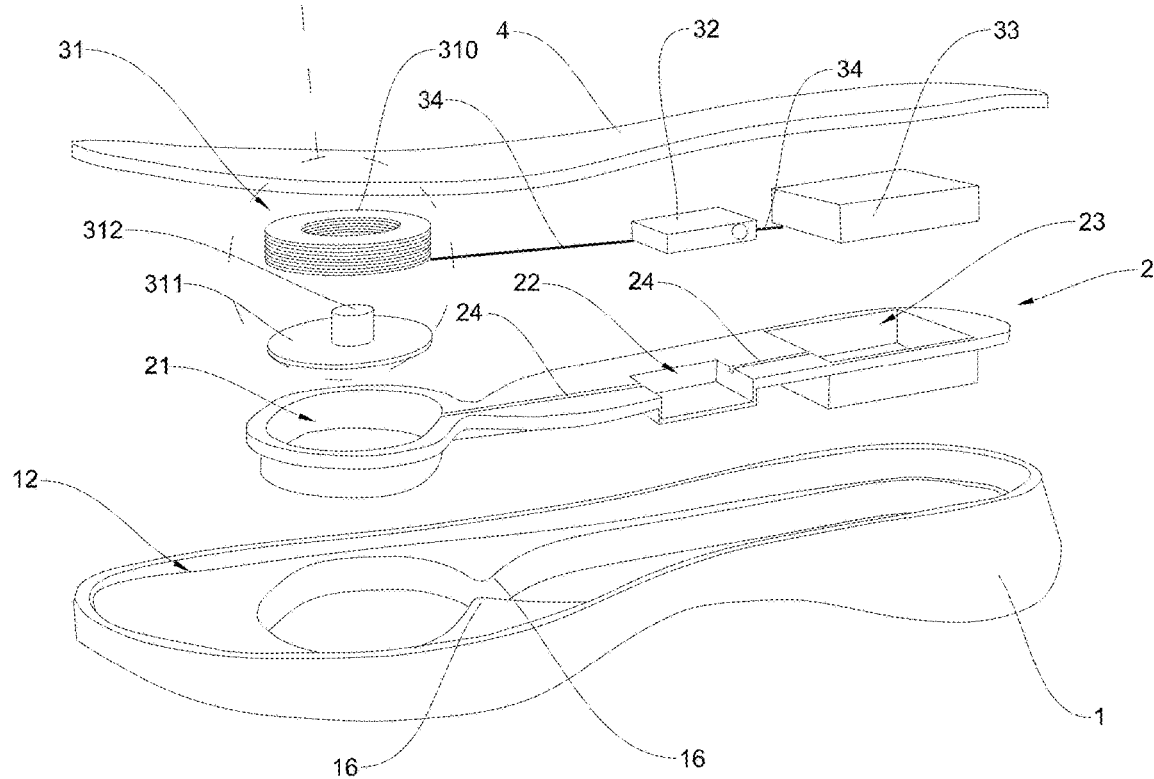

According to a preferred embodiment, the generator 31 comprises a winding 310, by means of which a magnetic field is generated following the passage of an alternating current. Preferably, as illustrated in FIGS. 3 and 3A, the winding 310 is supported by means of an insulating base 311 which comprises at the centre an elongate support 312 in order to maintain the winding 310 itself in a stable position.

In one embodiment, the winding 310 of the generator 31 is produced from aluminium, with advantages for the lightness of the structure. In association with this embodiment, the intermittent operation of the generator is found to be particularly advantageous because it allows the heating of the winding which is typically more intense if it is produced from aluminium to be constrained.

According to a preferred embodiment, the control unit 32 is of the programmable type. Preferably, the unit comprises a storage unit which is not illustrated in the Figures and which is capable of storing operating programmes of the magnetic field generator, in which the intensity of the magnetic field and the cyclical nature thereof can be varied in accordance with a time function. For example, the operation of the magnetic field may be similar to the one described in the international patent application WO 2015/004498.

In one embodiment, the control unit 32 comprises a wireless communication device 321 for controlling and/or programming the magnetotherapy cycles by means of a remote device, for example, a smartphone.

In one embodiment, the generator 31, the control unit 32 and the battery 33 are constructed as separate components and are mutually connected by means of one or more electrical conductors 34, as can be seen in FIG. 3.

Again with reference to FIG. 1, in one embodiment the intermediate container 2 is provided with a plurality of recesses which are intended to receive the generator 31, the control unit 32 and the battery 33, respectively. It should be noted that this characteristic advantageously allows the components for the magnetotherapy to be received in a precise manner, thereby ensuring ready assembly of the item of footwear. Preferably, the vamp structure 5 comprises blocking elements 51, for example, which are constructed in the form of transverse bands and are illustrated in FIG. 8A and which allow the arrangement of the intermediate container 2 together with the components responsible for the magnetotherapy in the region of the vamp structure 5.

In order to confer rigidity and at the same time stability, the intermediate container 2 may advantageously be constructed from a material having a greater rigidity than the one used for the lower sole.

By way of example, the material having greater rigidity of the intermediate container 2 can be formed by a block copolymer, such as an ABS nylon or an ether amide block copolymer, such as the one known under the commercial name Pebax®. Another alternative is constituted by a compact polyurethane, preferably thermosetting polyurethane (TPU). It is evident that these materials are provided merely by way of example and other alternatives may also be provided.

In one embodiment, the intermediate container 2 is provided with a covering element 20 so as to form a protective casing for receiving the battery, generator and control unit. Preferably, the container 2 and the other elements are received under reduced pressure inside the casing so as to ensure the adhesion of the casing and to improve the sealing with respect to moisture and dirt.

Optionally, there may be provided a pair of electric wires which are connected to the control unit and which extend out of the casing as far as the vamp so as to allow connection to a battery charger or other external devices.

Preferably, the intermediate container 2 and the covering element 20 are formed by a flexible film which is formed in such a manner as to define the recesses for receiving the components responsible for the magnetotherapy.

According to a preferred embodiment, the flexible film has a thickness between 0.3 and 0.6 mm.

In one embodiment, the intermediate container 2 and the covering element 20 are produced from thermosetting polyurethane.

The embodiment in which both the intermediate container 2 with the covering element 20 and the sole are produced from thermosetting polyurethane is particularly preferred because, as will be illustrated in greater detail below in relation to the production method of the item of footwear according to the present invention, it is possible to have optimum adhesion between the container and sole.

According to a preferred embodiment, the intermediate container 2 comprises three recesses 21, 22, 23.

Preferably, at least a first recess 21 is defined at the forefoot zone 101, at least a second recess 22 is defined in the mid-foot zone 102 and at least a third recess 23 is defined in the rear foot zone 103.

This characteristic optimally allows the space available in the item of footwear to be used. It is thereby possible to reduce the overall dimensions of the item of footwear, thereby allowing the production of an item of footwear which has good aesthetic characteristics and which at the same time is provided with magnetotherapeutic properties.

According to a preferred embodiment, the control unit 33 is arranged in the mid-foot zone 102. In one embodiment, however, the magnetic field generator 31, preferably together with the relevant insulating base 311, is received in the recess 21 of the forefoot zone 101 and the battery 33 is received in the recess of the rear foot zone 103. Preferably, the insulating base 311 has a form which complements the form of the recess 21, allowing stable accommodation of the generator 31.

Figure 5A:
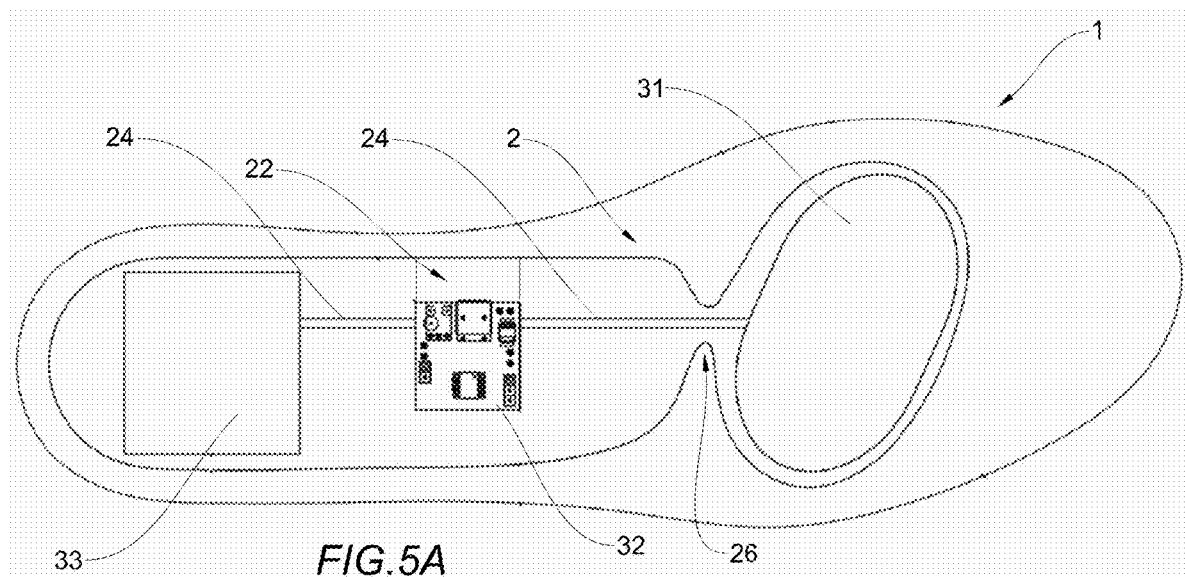
FIGS. 5A to 5C are schematic plan views of different embodiments of the item of footwear according to the present invention.
Figure 5B:
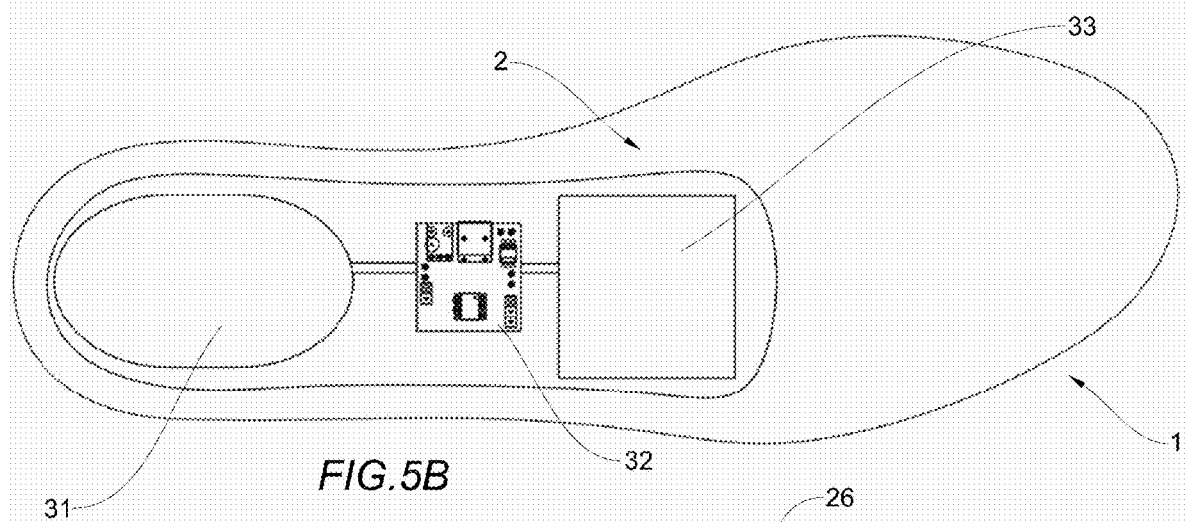

In an alternative embodiment, illustrated in FIG. 5B, the magnetic field generator 31 is arranged in the rear foot zone 103 and the battery 33 is received in the forefoot zone 101.

Figure 5C:
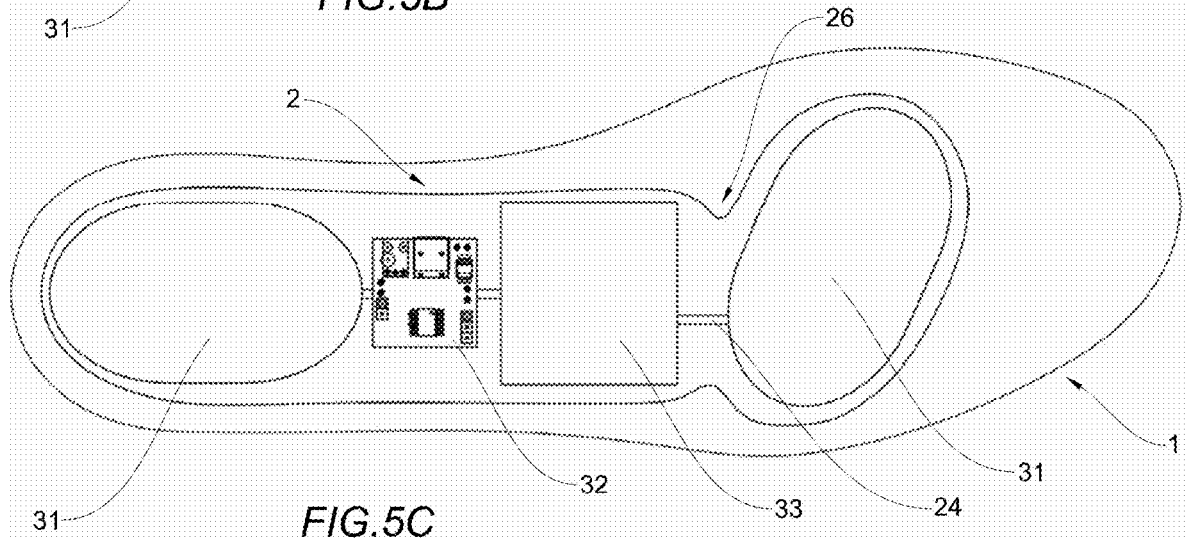

As another alternative, the battery 33 can also be arranged in the mid-foot zone 102, preferably in the region of the boundary with respect to the forefoot zone 101. In this manner, it is possible to allow the use of another magnetic field generator 31' which is arranged in the forefoot zone, as illustrated in FIG. 5C.

It may be noted that all the above-described arrangements allow the risk that the presence of the internal components may be noticed to be minimized. In fact, the control unit which typically is the smallest component, is in an intermediate position.

According to a preferred embodiment, the winding 311 of the magnetic field generator 31 is of elongate form.

Preferably, when the winding 311 is received in the forefoot zone, it is arranged transversely with respect to the longitudinal extent direction of the item of footwear.

Vice versa, when the winding is received in the rear foot zone, it is preferably arranged parallel with respect to the longitudinal extent direction of the item of footwear.

In both cases, there is obtained an optimum use of the available space, while ensuring adequate flexibility for the sole.

Figure 4:
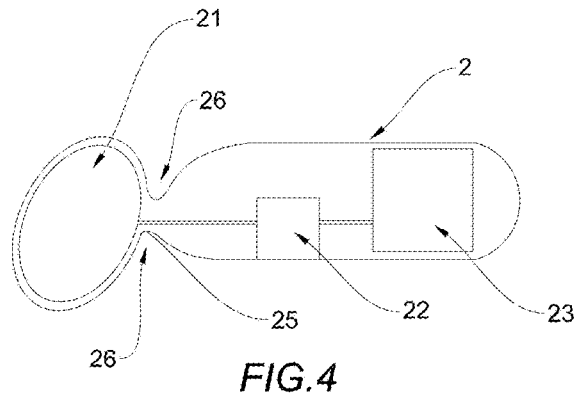
FIG. 4 is a top view of an intermediate container, of the item of footwear of FIG. 1.

With reference now to FIGS. 3 and 4, according to one embodiment the intermediate container 2 comprises passages 24 which are intended to receive, or more generally contain, the electrical conductors 34 which connect the battery, generator and control unit.

This characteristic advantageously allows the robustness of the structure to be increased, protecting the electrical connections in an adequate manner.

With reference now to FIG. 4, according to a preferred embodiment, the intermediate container 2 comprises a zone 25 having a reduced cross-section which is preferably positioned, when the container is in the relevant opening, at a transition region between the forefoot zone and the mid-foot zone, that is to say, in the region in which the flexion between those zones occurs during walking movement, as can be seen, for example, in FIG. 5A.

In one embodiment, the zone 25 having a reduced cross-section defines at least one blocking recess 26, preferably two, which engage(s) in respective widened portions 16 which are formed in the opening 12 and which are schematically illustrated in FIG. 5A.

It is thereby possible to also block the intermediate container in a longitudinal direction, increasing the assembly precision and the stability thereof, in particular during walking movement.

As can be seen in FIG. 3, the item of footwear 100 according to the present invention further comprises an inner sole 4 which is or can be positioned above the intermediate container 2 which is therefore arranged in an intermediate sole position.

The inner sole 4 can be constructed in accordance with the soles which are normally used in items of footwear, thereby providing the comfort required for the item of footwear. At the same time, the above-illustrated structure is also found to be readily able to be assembled, this being able to be carried out in successive steps.

Again with reference to FIG. 1, in one embodiment the lower sole 10 has a front portion 11 with reduced thickness such that, when the item of footwear is in abutment with the sole, this front portion 11 is spaced apart from the sole.

This allows an improvement in the walking movement, compensating for the thickness of the sole which is greater in relative terms than conventional items of footwear, that is to say, which are not provided with magnetotherapeutic functions.

According to a preferred embodiment, the front portion 11 with reduced thickness involves the lower sole over a distance between 30 mm and 70 mm from an end 11a of the tip of the item of footwear 100.

Preferably, the recesses are arranged externally at the front portion 11 with reduced thickness so as to prevent the internal components from being able to be subjected to greater risks of being damaged as a result of the presence of the front portion.

On the basis of optional aspects, the item of footwear according to the present invention further comprises an auxiliary magnetic field generator 34 which is positioned at a rear portion 53 of the vamp structure 5, as illustrated in FIG. 1.

Preferably, the rear portion 53 of the vamp is arranged in such a position as to face the Achilles tendon of the user when the item of footwear is worn, thereby allowing the generation of a magnetic field in a zone which is readily subjected to injuries and pains with a structurally simple solution.

According to another aspect, the present invention also relates to the method for producing the item of footwear described above.

This method is schematically illustrated in FIGS. 6 to 8B.

Initially with reference to FIG. 6, in one embodiment the intermediate container is formed by means of a flexible film 27 which is constructed by means of a premoulding of the film on a suitable preforming mould 6, which is provided with corresponding channels 61, 62 and 63 which correspond to the recesses 21, 22 and 23 which will be formed in the container.

As set out above, the film 27 is preferably constructed from a material suitable for being thermoformed.

The construction of the container is therefore carried out by closing the film 27 between the preforming mould 6 and a corresponding counter-mould 61.

The components which are responsible for the magnetotherapy are subsequently arranged in the container 2 which is constructed according to what has been indicated above or according to other methods, that is to say, in the above-described embodiment, the magnetic field generator 31, control unit 32 and battery 33 by means of the respective recesses.

With reference then to FIG. 7, the container 2 is preferably closed by means of the application of the covering element 20.

This operation can be carried out by positioning another flexible film, preferably having the same characteristics as the one used for producing the container 2 itself, with the components for magnetotherapy being positioned above the container 2, as illustrated in FIG. 7.

In this manner, by using an assembly mould 7 the container 2 can be sealed, obtaining a suitable protection for the components received therein.

Subsequently, and with reference to FIG. 8A, the container 2 is positioned on the vamp structure, preferably in the region of the inner sole 4. In order to simplify the positioning of the container, there can be used the blocking elements 51 set out above.

Finally, the lower sole is positioned on the vamp and on the container 2 which is positioned as described above.

The lower sole 1 can advantageously be constructed by means of an injection-moulding process, directly on the vamp structure. In this manner, the container 2 is directly blocked and surrounded on the lower sole 1, in which the opening 12 which is responsible for receiving the container directly after the moulding is defined.

According to a preferred embodiment, a thermosetting material is used for producing the sole, thereby allowing the construction by means of the process described above.

Using the same type of material for the sole and for the container is particularly preferred so that during the thermoforming of the sole there is produced a phenomenon of adhesion with respect to the container, thereby improving the compactness of the structure.

Therefore, the invention solves the problem set out, achieving at the same time a plurality of advantages, including the possibility of obtaining an item of footwear for magnetotherapy with optimum comfort characteristics.

In fact, using different materials allows the components required for the magnetotherapy to be adequately positioned and protected, even when using soles having a relatively small thickness.

In addition, the lower sole can advantageously be constructed by injection-moulding directly on the intermediate container, thereby also allowing the construction of complex structures, notwithstanding the presence of the components which are responsible for the magnetotherapy.

The presence of the inner sole further ensures a high level of comfort for the user, preventing at least partially the presence of the internal components from being noticed during use of the item of footwear.

The invention claimed is:

1. An item of footwear for magnetotherapy, comprising a lower sole in which there is defined a tread surface, an intermediate container which can be received in an opening which is defined in the lower sole a magnetic field generator, a control unit, a battery, an inner sole which is placed over the intermediate container and a vamp structure which is connected to the lower sole, wherein the intermediate container is formed as a single body and comprises respective recesses which are intended to receive the magnetic field generator, the control unit and the battery, respectively, wherein there are defined a forefoot zone, a mid-foot zone and a rear foot zone, and wherein the magnetic field generator is positioned in a first recess defined at the forefoot, the control unit is positioned in a second recess defined at the mid-foot and rear foot zones, and the battery is positioned in a third recess defined at the rear foot zone, the first recess, the second recess and the third recess are individually defined in each of the forefoot zone, the mid-foot zone and the rear foot zone.

2. The item of footwear according to claim 1, wherein the magnetic field generator, the control unit and the battery are connected by respective electrical conductors, the electrical conductors being received in respective passages defined in the intermediate container.

3. The item of footwear according to claim 1, wherein the lower sole has a front portion with reduced thickness so that, when the item of footwear is in abutment with ground, the front portion with reduced thickness is spaced apart from ground.

4. The item of footwear according to claim 3, wherein the front portion with reduced thickness involves the lower sole over a distance between 30 mm and 70 mm from an end of the tip of the item of footwear.

5. The item of footwear according to claim 3, wherein the recesses are arranged externally with respect to the front portion with reduced thickness.

6. The item of footwear according to claim 1, wherein the magnetic field generator comprises at least one winding of elongate form.

7. The item of footwear according to claim 6, wherein the winding is received in the forefoot zone and is arranged transversely with respect to a longitudinal extent direction (X) of the item of footwear.

8. The item of footwear according claim 1, further comprising an auxiliary magnetic field generator which is positioned at a rear portion of the vamp structure.

9. The item of footwear according to claim 8, wherein the rear portion of the vamp is arranged in such a position as to face an Achilles tendon of a user when the item of footwear is worn.

10. The item of footwear according to claim 1, wherein the intermediate container comprises a covering element which is positioned so as to form a protective casing, inside which one or more of the battery, generator and control unit is/are received.

11. The item of footwear according to claim 10, wherein the intermediate container and the covering element are formed by a flexible film.

12. The item of footwear according to claim 11, wherein the flexible film has a thickness between 0.3 and 0.6 mm.

13. The item of footwear according to claim 10, wherein the intermediate container and the covering element are produced from thermosetting material.

14. The item of footwear according to claim 1, wherein the intermediate container is formed by a material with greater rigidity, the intermediate container being formed by a block copolymer.

15. The item of footwear according to claim 1, wherein the intermediate container comprises a zone having a reduced cross-section which is positioned, when the container is in the relevant opening, at a transition region between the forefoot zone and the mid-foot zone.

16. The item of footwear according to claim 15, wherein the zone with a reduced cross-section defines at least one blocking recess which engages in a respective widened portion which is formed in the opening.

17. A method for producing an item of footwear for magnetotherapy according to claim 1, comprising:
   i. providing the vamp structure with the inner sole;
   ii. arranging the magnetic field generator, the control unit and the battery inside the respective recesses which are formed in the intermediate container;
   iii. positioning the intermediate container with the magnetic field generator, the control unit and the battery being received in the vamp structure in the region of the inner sole; and
   iv. injection-moulding the lower sole on the vamp structure with the intermediate container so as to form the opening.

18. The method according to claim 17, wherein the intermediate container is formed by moulding a flexible film.

19. The method according to claim 17, comprising pre-moulding the intermediate container so as to form the recesses which are configured for receiving the magnetic field generator, the control unit and the battery.

20. An item of footwear for magnetotherapy, comprising a lower sole in which there is defined a tread surface, an intermediate container which can be received in an opening which is defined in the lower sole a magnetic field generator, a control unit, a battery, an inner sole which is placed over the intermediate container and a vamp structure which is connected to the lower sole, wherein the intermediate container is formed as a single body and comprises respective recesses which are intended to receive the magnetic field generator, the control unit and the battery, respectively, wherein there are defined a forefoot zone, a mid-foot zone and a rear foot zone, and wherein the battery is positioned in a first recess defined at the forefoot, the control unit is positioned in a second recess defined at the mid-foot and rear foot zones, and the magnetic field generator is positioned in a third recess defined at the rear foot zone, the first recess, the second recess and the third recess are individually defined in each of the forefoot zone, the mid-foot zone and the rear foot zone.

* * * * *